(12) United States Patent
Sakai et al.

(10) Patent No.: US 10,418,665 B2
(45) Date of Patent: Sep. 17, 2019

(54) SEPARATOR ROLL, METHOD FOR PRODUCING SEPARATOR ROLL, AND LABEL CHECKING METHOD

(71) Applicant: Sumitomo Chemical Company, Limited, Tokyo (JP)

(72) Inventors: Akio Sakai, Daegu (KR); Yasutoshi Minemoto, Niihama (JP); Yusuke Kon, Daegu (KR)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 206 days.

(21) Appl. No.: 15/690,771

(22) Filed: Aug. 30, 2017

(65) Prior Publication Data

US 2018/0062209 A1  Mar. 1, 2018

(30) Foreign Application Priority Data

Aug. 31, 2016  (JP) .................. 2016-170105

(51) Int. Cl.

| H01M 10/0587 | (2010.01) |
|---|---|
| G01N 21/27 | (2006.01) |
| G01N 21/29 | (2006.01) |
| G06T 7/00 | (2017.01) |
| H01M 2/14 | (2006.01) |
| H01M 2/18 | (2006.01) |

(52) U.S. Cl.
CPC ........ *H01M 10/0587* (2013.01); *G01N 21/27* (2013.01); *G01N 21/29* (2013.01); *G06T 7/0008* (2013.01); *H01M 2/14* (2013.01); *H01M 2/145* (2013.01); *H01M 2/18* (2013.01)

(58) Field of Classification Search
CPC .... H01M 10/0587; H01M 2/14; H01M 2/145; H01M 2/18; G01N 21/27; G01N 21/29; G06T 7/0008
See application file for complete search history.

(56) References Cited

U.S. PATENT DOCUMENTS

| 7,960,048 | B2 * | 6/2011 | Jang ...................... H01M 2/046 429/174 |
|---|---|---|---|
| 2002/0164500 | A1* | 11/2002 | Scholtysik ............. B65H 19/29 428/838 |
| 2012/0164538 | A1* | 6/2012 | Inagaki ............... H01M 2/1653 429/249 |
| 2014/0322585 | A1 | 10/2014 | Iizuka et al. |

FOREIGN PATENT DOCUMENTS

| JP | 2013-139340 A | 7/2013 | |
|---|---|---|---|
| WO | WO-2016013462 A1 * | 1/2016 | ............. H01M 2/18 |

* cited by examiner

*Primary Examiner* — Gregg Cantelmo
(74) *Attorney, Agent, or Firm* — Panitch Schwarze Belisario & Nadel LLP

(57) ABSTRACT

A separator roll in accordance with an embodiment of the present invention includes a core, a heat-resistant separator wound around the core and in contact with an outer peripheral surface thereof, and a multilayer label attached to an outer layer surface of the heat-resistant separator, the multilayer label including a first film base and a second film base detachable from the first film base.

9 Claims, 12 Drawing Sheets

SEPARATOR ROLL, METHOD FOR PRODUCING SEPARATOR ROLL, AND LABEL CHECKING METHOD

This Nonprovisional application claims priority under 35 U.S.C. § 119 on Patent Application No. 2016-170105 filed in Japan on Aug. 31, 2016, the entire contents of which are hereby incorporated by reference.

TECHNICAL FIELD

The present invention relates to (i) a separator roll including a separator core and a separator for a nonaqueous electrolyte secondary battery (hereinafter referred to as a "nonaqueous electrolyte secondary battery separator") which separator is wound around the separator core and in contact with an outer peripheral surface thereof, (ii) a method for producing such a separator roll, and (iii) a label checking method.

BACKGROUND ART

Patent Literature 1 discloses an example of a separator core around which a separator is wound when being provided as a product, the separator having been produced continuously while being transferred via a transfer system such as a roller. The separator produced thusly is provided as a separator roll wound around an outer peripheral surface of the separator core. The separator roll is provided with a label attached to, for example, an inner peripheral surface of the separator core, the label (product label) showing information on the production of the separator (namely, the year, month, and day of the production, the lot number, and/or the like).

CITATION LIST

Patent Literature

[Patent Literature 1]
Japanese Patent Application Publication, Tokukai, No. 2013-139340 (Publication date: Jul. 18, 2013)

SUMMARY OF INVENTION

Technical Problem

When the separator is to be wound off from the separator core, a rotary shaft is inserted into the separator core to be in contact with the inner peripheral surface. In a case where a label has been attached to the inner peripheral surface of the separator core, friction between the label and the rotary shaft may, for example, wear off printed information on the label which information is on the production of the separator. This will unfortunately make it impossible to read, for example, production information shown by a label and identify information on the production of the separator used.

An embodiment of the present invention has been made in view of the above problem. An object of an embodiment of the present invention lies in facilitating identification of, for example, information on the production of a separator.

Solution to Problem

In order to attain the above object, a separator roll in accordance with an embodiment of the present invention includes: a separator core; a nonaqueous electrolyte secondary battery separator wound around the separator core and in contact with an outer peripheral surface of the separator core; and a multilayer label attached to an outer layer surface of the nonaqueous electrolyte secondary battery separator, the multilayer label including a plurality of film bases disposed on top of each other, the plurality of film bases including at least one film base detachable from another film base included in the plurality of film bases.

In order to attain the above object, a method in accordance with an embodiment of the present invention for producing a separator roll is a method for producing a separator roll including a separator core and a nonaqueous electrolyte secondary battery separator wound around the separator core and in contact with an outer peripheral surface of the separator core, the method including attaching a multilayer label to an outer layer surface of the nonaqueous electrolyte secondary battery separator wound around the separator core and in contact with the outer peripheral surface, the multilayer label including a plurality of film bases disposed on top of each other, the plurality of film bases including at least one film base detachable from another film base included in the plurality of film bases.

In order to attain the above object, a label checking method in accordance with an embodiment of the present invention is a method for checking a label attached to a separator roll including a separator core and a nonaqueous electrolyte secondary battery separator wound around the separator core and in contact with an outer peripheral surface of the separator core, the method including checking whether a multilayer label is attached to an outer layer surface of the nonaqueous electrolyte secondary battery separator wound around the separator core and in contact with the outer peripheral surface, the multilayer label including a plurality of film bases disposed on top of each other, the plurality of film bases including at least one film base detachable from another film base included in the plurality of film bases.

Advantageous Effects of Invention

The present invention advantageously makes it possible to easily check information on the production of a separator.

Figure 5:
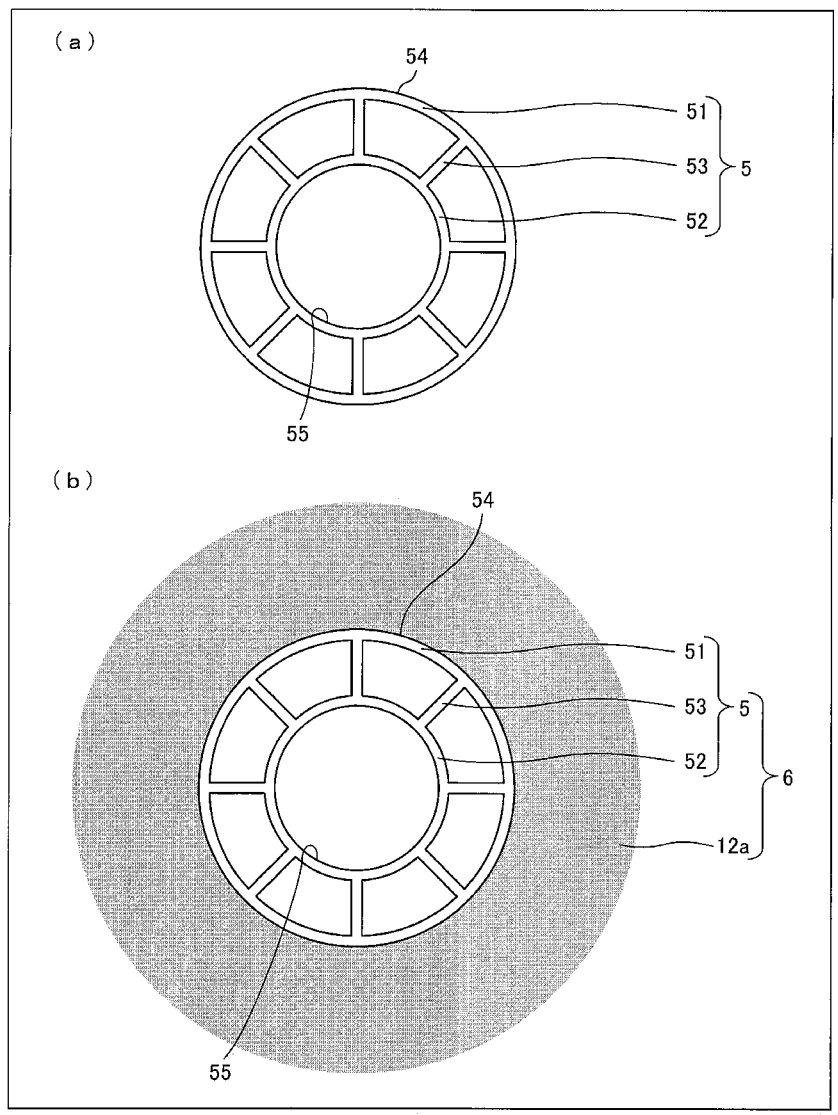

(a) of FIG. 5 is a side view of a core around which a heat-resistant separator is to be wound. (b) of FIG. 5 is a side view of an example of a separator roll in which a separator has been wound around the core illustrated in (a) of FIG. 5.

Figure 6:
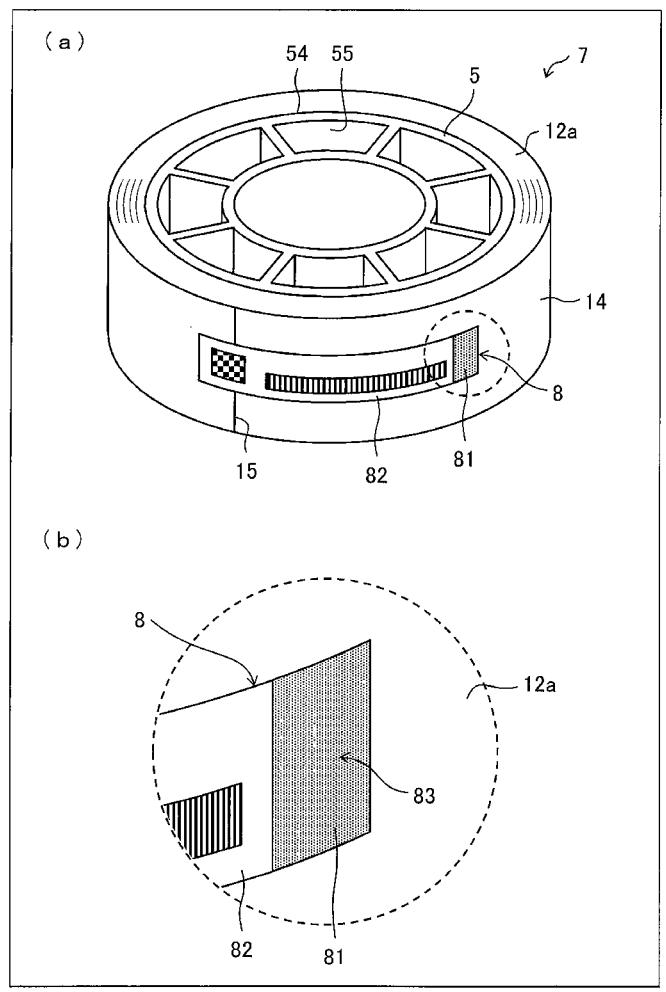

(a) of FIG. 6 is a perspective view of a separator roll in accordance with Embodiment 1. (b) of FIG. 6 is an enlarged view of a portion of the multilayer label illustrated in (a) of FIG. 6.

Figure 7:
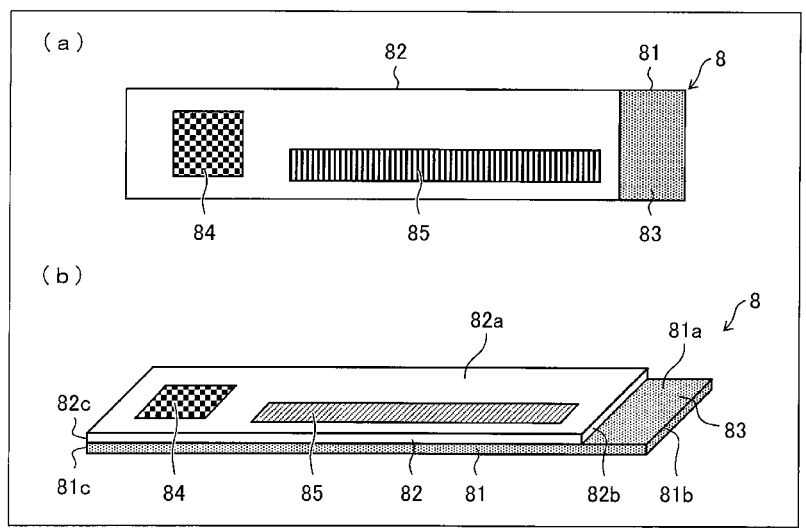

(a) of FIG. 7 is a plan view of the multilayer label illustrated in FIG. 6. (b) of FIG. 7 is a perspective view of the multilayer label illustrated in (a) of FIG. 7.

Figure 8:
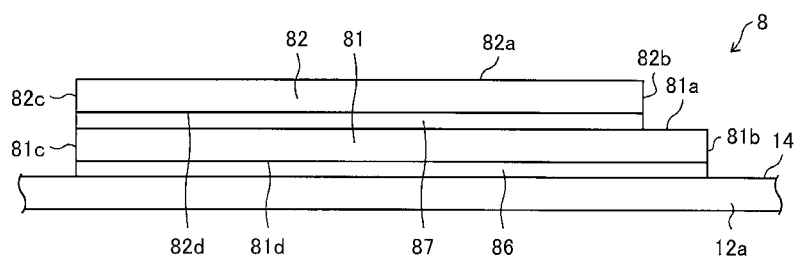

FIG. 8 is a cross-sectional view of the multilayer label illustrated in FIG. 7, the view illustrating a structure thereof including layers disposed on top of one another.

Figure 9:
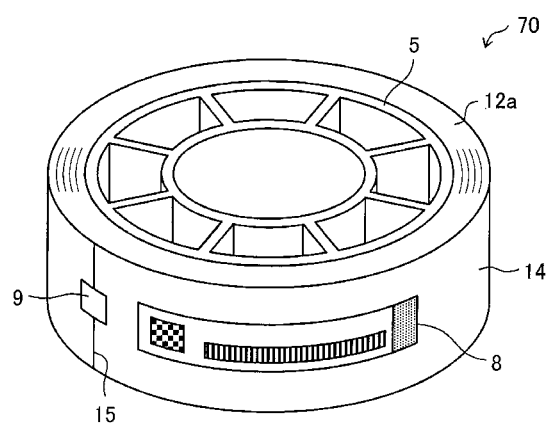

FIG. 9 is a perspective view of a variation of the separator roll illustrated in FIG. 6.

Figure 10:
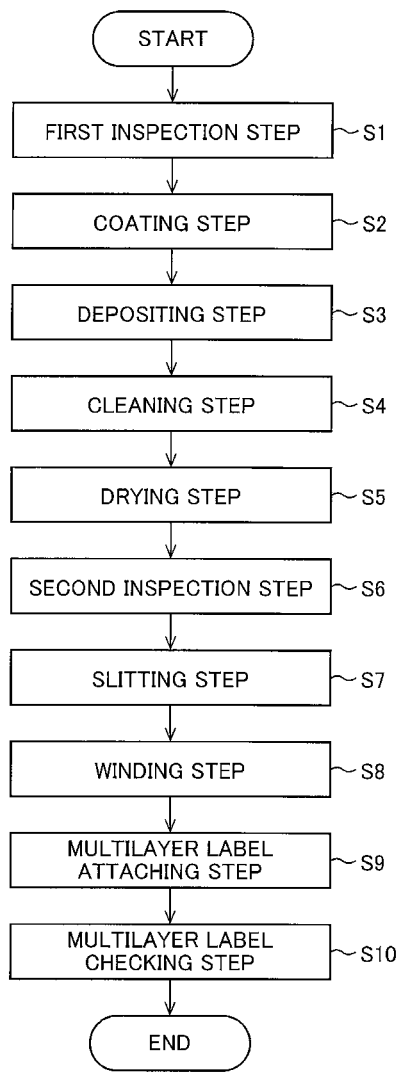

FIG. 10 is a flow chart schematically showing a method for producing a separator roll in accordance with Embodiment 2.

Figure 11:
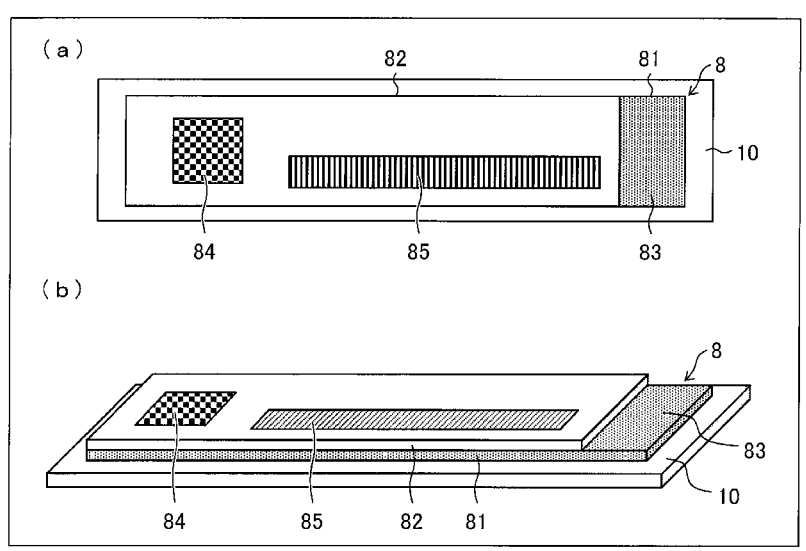

(a) of FIG. 11 is a plan view of an example multilayer label on a mount. (b) of FIG. 11 is a perspective view of the multilayer label illustrated in (a) of FIG. 11.

Figure 12:
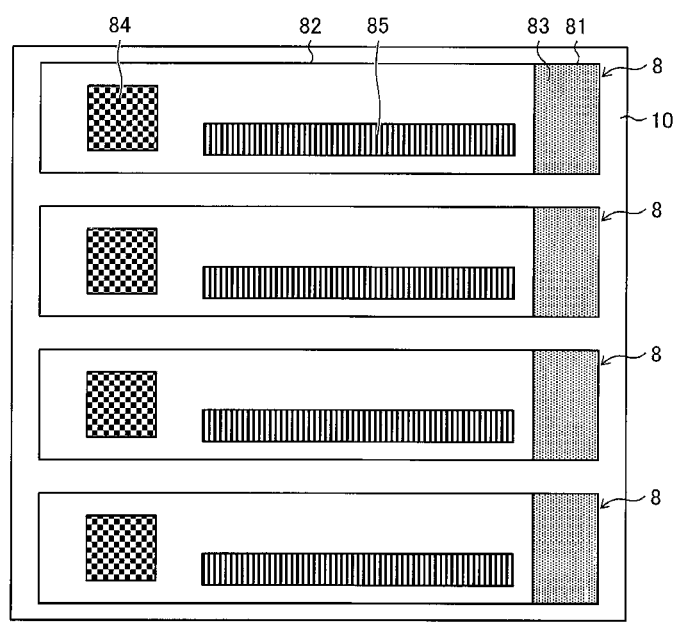

FIG. 12 is a plan view of another example of multilayer labels on a mount illustrated in FIG. 11.

Figure 13:
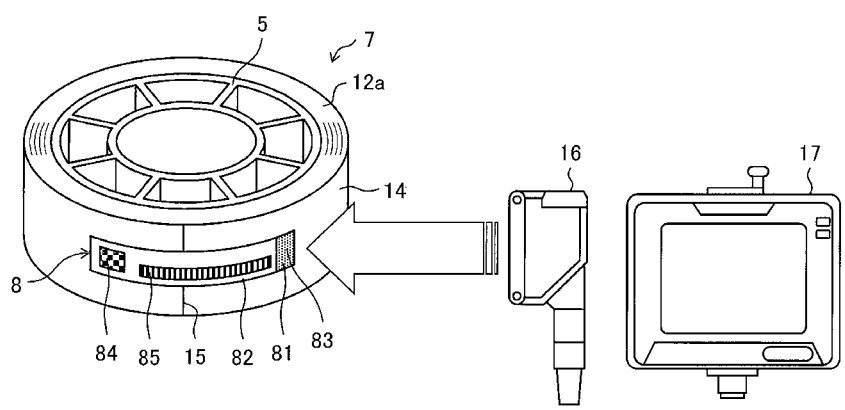

FIG. 13 is a diagram schematically illustrating an example of the multilayer label checking step illustrated in FIG. 10.

DESCRIPTION OF EMBODIMENTS

Embodiment 1

The following description will discuss an embodiment of the present invention with reference to FIGS. 1 to 9. Embodiment 1 described below is an example of a separator roll in accordance with an embodiment of the present invention which separator roll includes a separator core and a nonaqueous electrolyte secondary battery separator wound around the separator core.

The description below first deals with a lithium-ion secondary battery (nonaqueous electrolyte secondary battery) including a nonaqueous electrolyte secondary battery separator (hereinafter also referred to as a "separator") from a separator roll in accordance with Embodiment 1 which separator roll includes a separator core and a nonaqueous electrolyte secondary battery separator wound around the separator core.

<Configuration of Lithium-Ion Secondary Battery>

Figure 1:
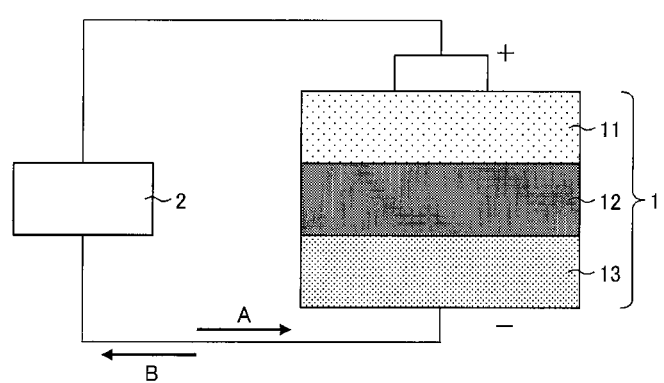
FIG. 1 is a diagram schematically illustrating a cross-sectional configuration of a lithium-ion secondary battery in accordance with Embodiment 1.
Figure 2:
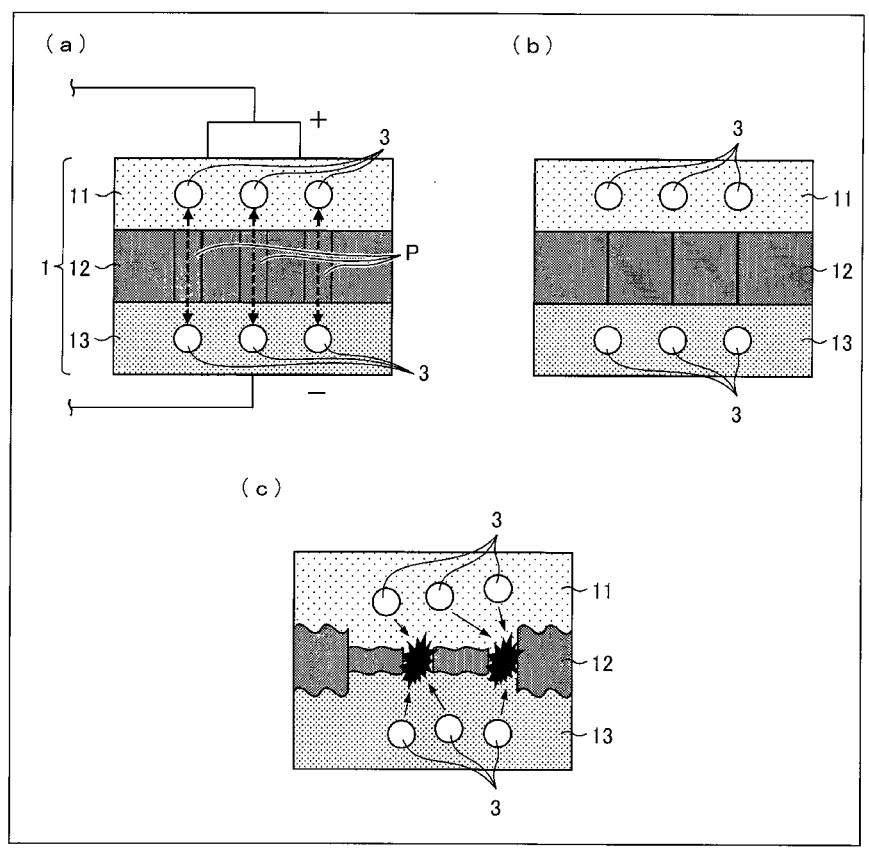
FIG. 2 provides diagrams schematically illustrating various states of the lithium-ion secondary battery illustrated in FIG. 1.
Figure 3:
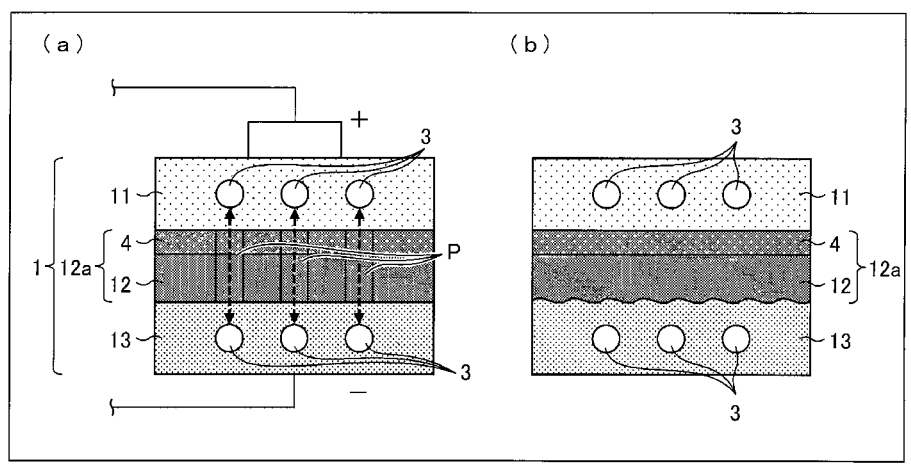
FIG. 3 provides diagrams schematically illustrating various states of a lithium-ion secondary battery having another configuration.

The following description will discuss a configuration of a lithium-ion secondary battery with reference to FIGS. 1 to 3. A nonaqueous electrolyte secondary battery, typically, a lithium-ion secondary battery has a high energy density, and therefore, is currently widely used not only as batteries for use in devices such as personal computers, mobile phones, and mobile information terminals, and for use in moving bodies such as automobiles and airplanes, but also as stationary batteries contributing to stable power supply.

FIG. 1 is a diagram schematically illustrating a cross sectional configuration of a lithium-ion secondary battery 1. As illustrated in FIG. 1, the lithium-ion secondary battery 1 includes a cathode 11, a separator 12, and an anode 13. Between the cathode 11 and the anode 13, an external device 2 is connected outside the lithium-ion secondary battery 1. Then, while the lithium-ion secondary battery 1 is being charged, electrons move in a direction A. On the other hand, while the lithium-ion secondary battery 1 is being discharged, electrons move in a direction B.

<Separator>

The separator 12 is provided so as to be sandwiched between the cathode 11 which is a positive electrode of the lithium-ion secondary battery 1 and the anode 13 which is a negative electrode of the lithium-ion secondary battery 1. The separator 12 separates the cathode 11 and the anode 13, allowing lithium ions to move between the cathode 11 and the anode 13. For example, polyolefin such as polyethylene or polypropylene is used as a material of the separator 12.

FIG. 2 provides diagrams schematically illustrating various states of the lithium-ion secondary battery 1 illustrated in FIG. 1. (a) of FIG. 2 illustrates a normal state. (b) of FIG. 2 illustrates a state in which a temperature of the lithium-ion secondary battery 1 has risen. (c) of FIG. 2 illustrates a state in which a temperature of the lithium-ion secondary battery 1 has sharply risen.

As illustrated in (a) of FIG. 2, the separator 12 is provided with many pores P. Normally, lithium ions 3 in the lithium-ion secondary battery 1 can move back and forth through the pores P.

However, there are, for example, cases in which the temperature of the lithium-ion secondary battery 1 rises due to excessive charging of the lithium-ion secondary battery 1, a high current caused by short-circuiting of the external device 2, or the like. In such cases, the separator 12 melts or softens and the pores P are blocked as illustrated in (b) of FIG. 2. As a result, the separator 12 shrinks. This stops the back-and-forth movement of the lithium ions 3, and consequently stops the above temperature rise.

However, in a case where a temperature of the lithium-ion secondary battery 1 sharply rises, the separator 12 suddenly shrinks. In this case, as illustrated in (c) of FIG. 2, the separator 12 may be destroyed. Then, the lithium ions 3 leak out from the separator 12 which has been destroyed. As a result, the lithium ions 3 do not stop moving back and forth. Consequently, the temperature continues rising.

<Heat-Resistant Separator>

FIG. 3 provides diagrams schematically illustrating various states of a lithium-ion secondary battery 1 having another configuration. (a) of FIG. 3 illustrates a normal state, and (b) of FIG. 3 illustrates a state in which a temperature of the lithium-ion secondary battery 1 has sharply risen.

As illustrated in (a) of FIG. 3, the lithium-ion secondary battery 1 can further include a heat-resistant layer 4. The heat-resistant layer 4 can be provided to the separator 12. (a) of FIG. 3 illustrates a configuration in which the separator 12 is provided with the heat-resistant layer 4 serving as a functional layer. A film in which the separator 12 is provided with the heat-resistant layer 4 is an example of a separator having a functional layer and is hereinafter referred to as a heat-resistant separator (film) 12a. In the separator having a functional layer, the separator 12 serves as a base material for the functional layer.

In the configuration illustrated in (a) of FIG. 3, the heat-resistant layer 4 is disposed on a surface of the separator 12 which surface is on a cathode 11 side. Note that the heat-resistant layer 4 can alternatively be disposed on a surface of the separator 12 which surface is on an anode 13 side, or both surfaces of the separator 12. Further, the heat-resistant layer 4 is provided with pores which are similar to the pores P. Normally, the lithium ions 3 move back and forth through the pores P and the pores of the heat-resistant layer 4. The heat-resistant layer 4 contains, for example, wholly aromatic polyamide (aramid resin) as a material.

As illustrated in (b) of FIG. 3, even in a case where the temperature of the lithium-ion secondary battery 1 sharply rises and as a result, the separator 12 melts or softens, the shape of the separator 12 is maintained because the heat-resistant layer 4 supports the separator 12. Therefore, such a sharp temperature rise results in only melting or softening of the separator 12 and consequent blocking of the pores P. This stops the back-and-forth movement of the lithium ions 3 and consequently stops the above-described excessive discharging or excessive charging. In this way, the separator 12 can be prevented from being destroyed.

<Steps of Producing Separator and Heat-Resistant Separator>

How to produce the separator 12 and the heat-resistant separator 12a of the lithium-ion secondary battery 1 is not particularly limited. The separator 12 and the heat-resistant separator 12a can be produced by a publicly known method. The following discussion assumes a case where a porous film serving as a raw material of the separator 12 (heat-resistant separator 12a) contains polyethylene as a main material. Note, however, that even in a case where the porous film contains another material, the separator 12 (heat-resistant separator 12a) can be produced by employing a similar production method.

Examples of the method for producing a porous film encompass a method which includes the steps of forming a film by adding inorganic filler or a plasticizer to a thermoplastic resin, and then removing the inorganic filler or the plasticizer by washing with an appropriate solvent. For example, in a case where the porous film is a polyolefin separator made of a polyethylene resin containing ultra-high molecular weight polyethylene, it is possible to produce the porous film by the following method.

This method includes (1) a kneading step of obtaining a polyethylene resin composition by kneading a ultra-high molecular weight polyethylene with (i) an inorganic filler (such as calcium carbonate or silica) or (ii) a plasticizer (such as low molecular weight polyolefin or fluid paraffin), (2) a rolling step of forming a film by means of the polyethylene resin composition, (3) a removal step of removing the inorganic filler or the plasticizer from the film obtained in the step (2), and (4) a stretching step of obtaining the porous film by stretching the film obtained in the step (3). The step (4) can be alternatively carried out between the steps (2) and (3).

In the removal step, many fine pores are formed in the film. The fine pores of the film stretched in the stretching step serve as the above-described pores P. The porous film (separator 12) is thus obtained. Note that the porous film is a polyethylene microporous film having a prescribed thickness and a prescribed air permeability.

Note that, in the kneading step, (i) 100 parts by weight of the ultra-high molecular weight polyethylene, (ii) 5 parts by weight to 200 parts by weight of a low molecular weight polyolefin having a weight-average molecular weight of 10000 or less, and (iii) 100 parts by weight to 400 parts by weight of the inorganic filler can be kneaded.

The heat-resistant separator 12a can be produced by disposing the heat-resistant layer 4, as a functional layer, on a surface of the separator 12 obtained as above. The functional layer is disposed on the separator 12 by (i) coating the separator 12 with a coating material (a material) corresponding to the functional layer and then (ii) drying the separator 12. Note that production of the heat-resistant separator 12a is discussed in detail in Embodiment 2, in a section discussing a method for producing a separator roll.

The separator 12, which does not include the heat-resistant layer 4, and the heat-resistant separator 12a (hereinafter also referred to as "separator") each preferably has a width (hereinafter referred to as "product width") suitable for application products such as the lithium-ion secondary battery 1. For improved productivity, however, a separator is produced so as to have a width that is equal to or greater than a product width. Then, after having been once produced so as to have a width equal to or larger than the product width, the separator is cut (slit) so as to have the product width and wound around a core (separator core).

Note that the expression "width of a/the separator" means a dimension of the separator in a direction that is parallel to a plane in which the separator extends and that is perpendicular to the longitudinal direction of the separator. Note also that (i) "slitting" means to slit the separator in the longitudinal direction (flow direction of the separator during production; MD: Machine direction) and (ii) "cutting" means to slit the separator in a transverse direction (TD). Furthermore, "transverse direction (TD)" means a direction that is parallel to a plane in which the separator extends and that is substantially perpendicular to the longitudinal direction (MD) of the separator. Hereinafter, a wide separator which has not been subjected to slitting is also referred to as an "original sheet."

Figure 4:
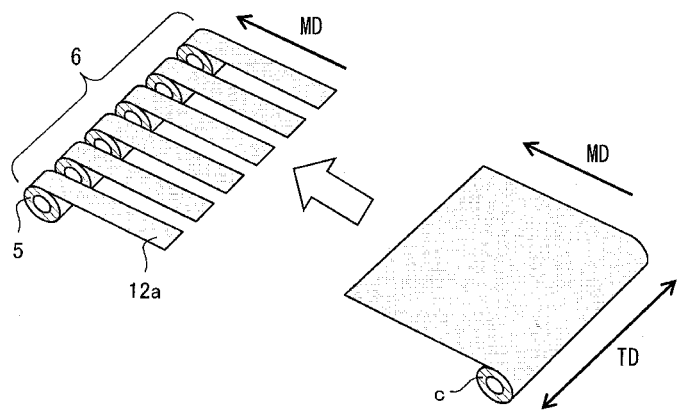
FIG. 4 is a diagram schematically illustrating an example of a winding step in which a separator which has been slit is wound around a core.

FIG. 4 is a diagram schematically illustrating an example of a winding step in which a heat-resistant separator 12a which has been slit is wound around a core 5. As illustrated in FIG. 4, an original sheet of the heat-resistant separator 12a, being transferred in the machine direction, is slit so as to be divided into a plurality of heat-resistant separators 12a having a predetermined product width. The plurality of the heat-resistant separators 12a are each wound around a respective core (separator core) 5 having a cylindrical shape. Note that a combination of (i) a separator (separator 12 or heat-resistant separator 12a) wound into a roll form and (ii) the core 5 is referred to as a separator roll 6.

<Structure of Separator Roll>

The following description will first discuss a configuration of the core 5 with reference to FIG. 5. (a) of FIG. 5 is a side view of the core 5. (b) of FIG. 5 is a side view of an example of a separator roll 6 in which a separator has been wound around the core 5 illustrated in (a) of FIG. 5. Note that (b) of FIG. 5 illustrates an example in which the separator roll 6 is constituted by the heat-resistant separator 12a wound around the core 5.

As illustrated in (a) of FIG. 5, the core 5 includes an outer cylindrical member 51, an inner cylindrical member 52, and a plurality of ribs 53. The outer cylindrical member 51 is a cylindrical member around which a separator is wound to be in contact with an outer peripheral surface 54. The inner cylindrical member 52 is a cylindrical member that is provided inward of the outer cylindrical member 51 and that functions as a bearing configured to receive a rotary shaft for rotating the core 5 (such as a wind-up roller and a wind-off roller) on an inner peripheral surface 55. Each of the ribs 53 extends between the outer cylindrical member 51 and the inner cylindrical member 52 in a diametral direction and serves as a supporting member connecting the two. In Embodiment 1, the ribs 53 are provided so as to have equal intervals therebetween, at respective positions dividing the circumference of the core into eight equal portions. Each of the ribs 53 is provided so as to be substantially perpendicular to both the outer cylindrical member 51 and the inner cylindrical member 52. Note that the number of ribs 53 and the placement interval of the ribs 53 are not limited to the above configuration.

The respective central axes of the outer cylindrical member 51 and the inner cylindrical member 52 preferably substantially match each other but are not limited to such a configuration. Furthermore, dimensions of the outer cylindrical member 51 and the inner cylindrical member 52, such as the respective thicknesses, widths, and radii thereof, can be designed as appropriate in accordance with, for example, the type of separator to be wound.

With regards to a material of the core 5, a resin containing any of ABS resin, polyethylene resin, polypropylene resin, polystyrene resin, polyester resin, and a vinyl chloride resin can be suitably used. This makes it possible to produce the core 5 by resin molding which uses a metal mold.

As illustrated in (b) of FIG. 5, the separator roll 6 is constituted by a separator (heat-resistant separator 12*a*) that has been slit into the product width and wound into the form of a roll around an outer peripheral surface 54 of the core 5 (that is, around the outer peripheral surface 54 of the outer cylindrical member 51).

The separator roll 6 is provided with a label (product label) attached thereto that shows information (product information) on the production of the separator around the core 5 before the separator roll 6 is supplied.

With conventional art, a label would be attached to, for example, the inner peripheral surface 55 of a core 5 (that is, the inner peripheral surface 55 of an inner cylindrical member 52). In a case where a label has been attached to the inner peripheral surface 55 of a core 5, since a rotary shaft is inserted into the core 5 to be in contact with the inner peripheral surface 55 for winding off the separator from the core 5, friction between the label and the rotary shaft may, for example, wear off printed information on the label (product information) which information is on the production of the separator. This will unfortunately make it impossible to read, for example, production information shown by a label and identify information on the production of the separator used. In a case where a label has been attached to the outer layer surface 14 of a separator roll 6, since the label is attached to the separator, winding off the separator for consumption will unfortunately cause information on the production of the separator to be lost as well. Embodiment 1 solves this issue by using a multilayer label including film bases that are detachably disposed on top of each other.

<Description of Multilayer Label>

(a) of FIG. 6 is a perspective view of a separator roll 7 in accordance with Embodiment 1. (b) of FIG. 6 is an enlarged view of a portion of the multilayer label 8 illustrated in (a) of FIG. 6.

As illustrated in (a) of FIG. 6, the separator roll 7 includes a core 5, a heat-resistant separator 12*a*, and a multilayer label 8. The separator roll 7 corresponds to a separator roll 6 of (b) of FIG. 5 provided with a multilayer label 8 attached thereto.

The multilayer label 8 is a label (product label) that shows information on the production of the heat-resistant separator 12*a*. The multilayer label 8 is attached to the outer layer surface 14 of the heat-resistant separator 12*a* wound around the core 5.

The multilayer label 8 of Embodiment 1 has the shape of a rectangle (oblong) having long sides extending along the longitudinal direction of the heat-resistant separator 12*a* wound around the core 5. The shape of the multilayer label 8 is, however, not limited to a rectangle, but may alternatively be another shape (for example, a polygon such as a square or a circle).

The multilayer label 8 is attached to the outer layer surface 14 of the heat-resistant separator 12*a* in such a manner as to extend across a longitudinal end (short side) 15 of the heat-resistant separator 12*a*. This allows the end 15 of the heat-resistant separator 12*a* to be fastened with use of the multilayer label 8. The use of the multilayer label 8 eliminates the need to separately use a fastening sticker 9 (see FIG. 9) to fix the end 15, thereby making it possible to omit the fastening sticker 9.

The multilayer label 8 in accordance with Embodiment 1 is structured to include a first film base 81 and a second film base 82 that are detachably disposed (bonded) on top of each other. The first film base 81 is bonded to the heat-resistant separator 12*a*, and functions as a mount for the second film base 82. The second film base 82 is disposed on the first film base 81, and has the function of displaying information on the production of the heat-resistant separator 12*a*. The number of film bases included in the multilayer label 8 is not limited to two; the multilayer label 8 may include three or more film bases disposed on top of one another. The number of film bases included in the multilayer label 8 may be changed as appropriate depending on, for example, the purpose of use of the multilayer label 8.

As illustrated in (b) of FIG. 6, the multilayer label 8 has a residue-removed portion 83 at a first one of the ends of the multilayer label 8 that are opposite to each other longitudinally. The first film base has a front surface 81*a*, which is partially exposed at the residue-removed portion 83.

The term "residue removing" as used herein refers to an operation of removing unnecessary part (that is, part other than the label) of adhesive paper after half-cutting the multilayer label. A residue-removed portion is a portion from which unnecessary adhesive paper has been removed.

(a) of FIG. 7 is a plan view of the multilayer label 8 illustrated in FIG. 6. (b) of FIG. 7 is a perspective view of the multilayer label 8 illustrated in (a) of FIG. 7. As illustrated in (a) and (b) of FIG. 7, the second film base 82 has a front surface 82*a* provided with, printed thereon, a QR Code (registered trademark) 84 indicative of information on the production of the heat-resistant separator 12*a*, a bar code 85, and/or the like. Information on the production includes various information items such as the year, month, and day of the production, lot number, material, size, weight, length, front/back side, and/or packing number of the heat-resistant separator 12*a*. The front surface 81*a* of the first film base 81 may also be provided with, printed thereon, a QR Code (registered trademark) 84, a bar code 85, and/or the like.

As described above, the multilayer label 8 has a residue-removed portion 83 at a first one of the ends of the multilayer label 8 that are opposite to each other lengthwise, at which residue-removed portion 83 the front surface 81*a* is exposed on the side of a first end 81*b* of the first film base 81. In other words, the multilayer label 8 is configured such that the first film base 81 has long sides that are longer than the long sides of the second film base 82 and that the first film base 81 has short sides that are equal in length to the short sides of the second film base 82. Thus, the first film base 81 has (i) a first end 81*b* that extends more outwards than a first end 82*b* of the second film base 82 and (ii) a second end 81*c* that coincides with a second end 82*c* of the second film base 82. Forming a residue-removed portion 83 in a multilayer label 8 makes it possible to, in a case where, for instance, someone handles the separator roll 7 with gloves on, easily peel the second film base 82 off from the first film base 81 by peeling the second film base 82 from the side of the residue-removed portion 83.

The multilayer label 8 may alternatively have a residue-removed portion 83 at each of the ends opposite to each other lengthwise. The multilayer label 8 may alternatively be configured such that the short sides of the first film base 81 are different in length from the short sides of the second film base 82.

The multilayer label 8 is configured such that the first film base 81 has a color different from the color of the second film base 82. For instance, the first film base 81 is a blue film base, whereas the second film base 82 is a white film base.

This makes it easy to visually or in another manner distinguish the first film base 81 (which is blue) exposed at the residue-removed portion 83. Further, the heat-resistant separator 12a may have a color different from the color of the first film base 81. This makes it easier to distinguish the first film base 81 exposed at the residue-removed portion 83.

FIG. 8 is a cross-sectional view of a multilayer label 8, the view illustrating a structure thereof including layers disposed on top of one another. FIG. 8 omits the end 15 of a heat-resistant separator 12a. As illustrated in FIG. 8, the multilayer label 8 includes a first adhesive layer 86, a first film base 81, a second adhesive layer 87, and a second film base 82 that are all disposed on top of one another in this order from the side of the outer layer surface 14 of the heat-resistant separator 12a.

The first adhesive layer 86 is a layer made of an adhesive and present on a back surface 81d of the first film base 81. With the first adhesive layer 86, the multilayer label 8 is bonded to the outer layer surface 14 of the heat-resistant separator 12a.

The second adhesive layer 87 is a layer made of an adhesive and present on the side of a back surface 82d of the second film base 82. With the second adhesive layer 87, the second film base 82 is disposed detachably on the front surface 81a of the first film base 81. This allows the second film base 82 to be easily peeled off from the first film base 81. With this arrangement, a heat-resistant separator 12a can, for example, be stored with the second film base 82 peeled off from the first film base 81 before the heat-resistant separator 12a is wound off from the core 5, so that information on the production of the heat-resistant separator 12a can be easily obtained. When the second film base 82 has been peeled off from the first film base 81, the second adhesive layer 87 remains on the back surface 82d of the second film base 82. This makes it possible to attach the peeled second film base 82 to a position easily noticeable.

<Recap of Description of Separator Roll>

As described above, a separator roll 7 in accordance with Embodiment 1 includes a core 5, a heat-resistant separator 12a wound around the core 5 and in contact with an outer peripheral surface 54 thereof, and a multilayer label 8 attached to an outer layer surface 14 of the heat-resistant separator 12a, the multilayer label 8 including a first film base 81 and a second film base 82 detachable from the first film base 81.

Embodiment 1 is thus a separator roll 7 that allows easy identification of, for example, information on the production of a heat-resistant separator 12a.

<Variations>

FIG. 9 is a perspective view of a variation of the separator roll in accordance with Embodiment 1. FIG. 9 illustrates a separator roll 70 including a core 5, a heat-resistant separator 12a, a multilayer label 8, and a fastening sticker 9.

The fastening sticker 9 is a sticker for fastening a longitudinal end 15 of the heat-resistant separator 12a wound around the core 5 which end 15 is at the outer layer surface 14. The separator roll 70 includes a fastening sticker 9 as a member separate from the multilayer label 8. This increases the degree of freedom in where to attach the multilayer label 8. The above configuration further makes it possible to attach a multilayer label 8 and a fastening sticker 9 at respective time points different from each other. For instance, the above configuration makes it possible to attach (i) a fastening sticker 9 during the step of winding up a heat-resistant separator 12a and (ii) a multilayer label 8 during a multilayer label attaching step after the winding step. The above configuration thus makes it possible to attach the multilayer label 8 and the fastening sticker 9 at respective appropriate time points different from each other.

Embodiment 2

The following description will discuss another embodiment of the present invention with reference to FIGS. 10 and 13. Embodiment 2 described below is an example of a method for producing a separator roll 7 described in Embodiment 1 above.

<Method for Producing Separator Roll>

FIG. 10 is a flow chart schematically showing a method for producing the separator roll 7 in accordance with Embodiment 2. The heat-resistant separator 12a to be wound around the core 5 is configured to include (i) the separator 12 and (ii) the heat-resistant layer 4 disposed on the separator 12 as a functional layer. The heat-resistant separator 12a is obtained by (i) forming the heat-resistant layer 4 on a surface of an original sheet of the separator 12 which serves as a base material, the separator 12 being transferred via a transfer system such as a roller, and (ii) subsequently slitting the separator 12, having the heat-resistant layer 4 thereon, so as to have a product width.

In the method shown exemplarily, a wholly aromatic polyamide (aramid resin) is used as a coating material which forms the heat-resistant layer 4. The method includes a step of disposing the heat-resistant layer 4 on the original sheet of the separator 12 (such an original sheet hereinafter also referred to as a "separator original sheet").

Specifically, the method includes a first inspection step S1, a coating step S2, a depositing step S3, a cleaning step S4, a drying step S5, a second inspection step S6, a slitting step S7, a winding step S8, a multilayer label attaching step S9, and a multilayer label checking step S10. Each of the steps S1 through S10 will be discussed below in order.

(First Inspection Step)

The first inspection step S1 is a step of inspecting the separator original sheet, which will serve as the base material of the heat-resistant separator 12a, in order to determine, prior to subsequent steps, whether or not there is a defect in the separator original sheet.

(Coating Step)

The coating step S2 is a step of coating, with a coating material (a material) for the heat-resistant layer 4, the separator original sheet which has been inspected in the first inspection step S1. In the coating step S2, it is possible to carry out the coating with respect to only one surface of the separator original sheet or both surfaces of the separator original sheet.

For example, in the coating step S2, the separator original sheet is coated with an aramid/NMP (N-methyl-pyrrolidone) solution, as the coating material for the heat-resistant layer 4. Note that the heat-resistant layer 4 is not limited to an aramid heat-resistant layer. For example, a mixed solution containing a filler such as alumina/carboxymethyl cellulose can be applied as the coating material for the heat-resistant layer 4.

A method for coating the separator original sheet with the coating material is not specifically limited as long as uniform wet coating can be performed with respect to the separator original sheet by the method, and various methods can be employed.

For example, it is possible to employ any of the methods such as a capillary coating method, a slit die coating method, a spray coating method, a dip coating method, a roll coating method, a screen printing method, a flexo printing method, a bar coater method, a gravure coater method, or a die coater method.

A coating material for the heat-resistant layer 4 with which material the separator original sheet is coated has a film thickness that can be controlled by adjusting a thickness of a coating wet film and a solid-content concentration in the coating solution.

(Depositing Step)

The depositing step S3 is a step of solidifying the coating material with which the separator original sheet has been coated in the coating step S2. In a case where the coating material is an aramid coating material, for example, water vapor is applied to a coated surface so that aramid is solidified by humidity deposition.

(Cleaning Step)

The cleaning step S4 is a step of cleaning the separator original sheet on which the coating material has been solidified in the depositing step S3 (such a separator original sheet hereinafter also referred to as a "heat-resistant separator original sheet"). In a case where the heat-resistant layer 4 is an aramid heat-resistant layer, for example, water, an aqueous solution, or an alcohol-based solution is suitably used as a cleaning liquid.

Note that the cleaning step S4 can be multistage cleaning in which cleaning is carried out a plurality of times in order to enhance a cleaning effect. Moreover, after the cleaning step S4, a water removing step can be carried out for removing water from the heat-resistant separator original sheet which has been cleaned in the cleaning step S4. A purpose of the water removing is to remove water or the like that is adhered to the heat-resistant separator original sheet before the subsequent drying step S5 so that drying can be carried out more easily and insufficient drying can be prevented.

(Drying Step)

The drying step S5 is a step of drying the heat-resistant separator original sheet that has been cleaned in the cleaning step S4. A method for drying the heat-resistant separator original sheet is not particularly limited, and, for example, it is possible to use various methods such as a method in which the heat-resistant separator original sheet is brought into contact with a heated roller or a method in which hot air is blown onto the heat-resistant separator original sheet.

(Second Inspection Step)

The second inspection step S6 is a step of inspecting the heat-resistant separator original sheet which has been dried in the drying step S5. In the inspection, a defect is marked as appropriate, and it is therefore possible to effectively inhibit the heat-resistant separator original sheet from having a defect.

(Slitting Step)

The slitting step S7 is a step of slitting (cutting) the heat-resistant separator original sheet which has been inspected in the second inspection step S6 into parts each having a predetermined product width. Specifically, in the slitting step S7, the heat-resistant separator original sheet is slit into parts each having a product width which is suitable for an applied product such as the lithium-ion secondary battery 1.

As described above, in order to increase productivity, a heat-resistant separator original sheet is usually produced so as to have a width that is equal to or greater than the product width. The heat-resistant separator 12*a* is therefore obtained by slitting the separator original sheet, in the slitting step S7, so as to have the product width.

(Winding Step)

The winding step S8 is a step of winding the heat-resistant separator 12*a*, which is as slit in the slitting step S7 so as to have the product width, around the core 5 having a cylindrical shape. Carrying out the winding step S8 produces a separator roll including an integrated combination of a core 5 and a heat-resistant separator 12*a* wound around the core 5 into a roll.

(Multilayer Label Attaching Step S9)

The multilayer label attaching step S9 is a step of attaching a multilayer label 8 that shows information on the production of the heat-resistant separator 12*a* wound up around the core 5 in the slitting step S7. The multilayer label attaching step S9 of Embodiment 2 is a step of attaching a multilayer label 8 to an outer layer surface 14 of the heat-resistant separator 12*a* (which is wound around the core 5 and in contact with an outer peripheral surface 54 thereof) in such a manner that the multilayer label 8 extends across an end 15 of the heat-resistant separator 12*a*.

(a) of FIG. 11 is a plan view of an example multilayer label 8 on a mount 10. (b) of FIG. 11 is a perspective view of the multilayer label 8 illustrated in (a) of FIG. 11. As illustrated in (a) and (b) of FIG. 11, a multilayer label 8 before attachment is on a mount (release paper) 10 and has an end portion removed. When the multilayer label 8 is to be peeled off from the mount 10, peeling the multilayer label 8 off from the side of a second end of the multilayer label 8 at which second end no residue-removed portion 83 is present can prevent erroneous attachment such as erroneously peeling only the second film base 82 off and attaching it to the outer layer surface 14 of the heat-resistant separator 12*a*. The multilayer label 8 thus preferably has a residue-removed portion 83 at only one of the ends opposite to each other lengthwise.

FIG. 12 is a plan view of another example of multilayer labels 8 on a mount 10 illustrated in FIG. 11. As illustrated in FIG. 12, a plurality of multilayer labels 8 may be on a single mount 10. Even in such a case, peeling each multilayer label 8 off from the side of a second end of the multilayer label 8 at which second end no residue-removed portion 83 is present can prevent erroneous attachment described above.

Attaching a multilayer label 8 to the outer layer surface 14 of the heat-resistant separator 12*a* in the multilayer label attaching step S9 is easier than attaching a label to the inner peripheral surface 55 of a core 5 as in conventional art. The above arrangement can thus shorten the operation time necessary to attach a label. The above arrangement also eliminates the need to, for example, detach the label from the inner peripheral surface 55 of the core 5 after use, thereby making it easy to, for example, clean the core 5.

(Multilayer Label Checking Step S10)

The multilayer label checking step (label checking method) S10 is a step of checking the multilayer label 8 attached to the heat-resistant separator 12*a* in the multilayer label attaching step S9. In the multilayer label checking step S10, whether a multilayer label 8 is attached to the heat-resistant separator 12*a* appropriately is checked either visually or with use of a sensor. Using a blue or otherwise colored film base as the first film base 81 of a multilayer label 8 will facilitate checking the multilayer label 8 visually or with use of a sensor.

FIG. 13 is a diagram schematically illustrating an example of the multilayer label checking step S10. As illustrated in FIG. 13, the multilayer label checking step S10 may be carried out by, for example, equipping an automated packing machine with, for example, a sensor 16 and a monitor 17 for automatic sensing of erroneous attachment of a multilayer label 8.

In this case, comparing (i) an image detected by the sensor 16 with (ii) a preregistered reference image makes it possible to sense whether a multilayer label 8 is attached to the outer layer surface 14 of the heat-resistant separator 12*a* appropriately. For instance, determining on the basis of the position of a bar code 85 on a multilayer label 8 in an image detected by the sensor 16 whether the first end 81*b* of the first film base 81 is present at a predetermined position makes it possible to sense whether a multilayer label 8 is present or displaced.

Alternatively, whether a multilayer label 8 is present or displaced may be sensed by sensing the front surface 81*a* of the first film base 81 which front surface 81*a* is exposed at a residue-removed portion 83 of the multilayer label 8. In this case, sensing the front surface 81*a* of the first film base 81 with use of a color sensor as the sensor 16 and analyzing the area and/or the like of the front surface 81*a* makes it possible to sense whether a multilayer label 8 is present or displaced.

The multilayer label 8, which is attached to the outer layer surface 14 of the heat-resistant separator 12*a*, is easier to read than a label attached to the inner peripheral surface 55 of a core 5 as in conventional art. The above arrangement can thus shorten the operation time necessary to read a label. Simultaneously checking and reading a label will make it possible to rapidly link the production information and the checking result.

After having undergone the multilayer label checking step S10 described above, the separator roll 7 is supplied as a product.

SUPPLEMENTAL NOTES

A separator roll in accordance with an embodiment of the present invention includes: a separator core; a nonaqueous electrolyte secondary battery separator wound around the separator core and in contact with an outer peripheral surface of the separator core; and a multilayer label attached to an outer layer surface of the nonaqueous electrolyte secondary battery separator, the multilayer label including a plurality of film bases disposed on top of each other, the plurality of film bases including at least one film base detachable from another film base included in the plurality of film bases.

With the above configuration, a multilayer label is attached to the outer layer surface of a nonaqueous electrolyte secondary battery separator wound around a separator core and in contact with the outer peripheral surface thereof. This prevents information printed on a label from becoming unreadable as a result of the label being, as in a case where a label has been attached to the inner peripheral surface of a separator core, detached due to friction between the inner peripheral surface and a rotary shaft. Further, the plurality of film bases include at least one film base detachable from another film base included in the plurality of film bases. With this configuration, the nonaqueous electrolyte secondary battery separator can, for example, be stored with a film base(s) peeled off from the multilayer label before the nonaqueous electrolyte secondary battery separator is wound off from the separator core, so that information such as information on the production of the separator can be easily identified.

The above configuration thus makes it possible to produce a separator roll that allows easy identification of, for example, information on the production of the separator.

A separator roll in accordance with an embodiment of the present invention may be configured such that the plurality of film bases includes (i) a first film base to be bonded to the outer layer surface and (ii) a second film base disposed detachably on the first film base and showing information on the nonaqueous electrolyte secondary battery separator; and a front surface of the first film base is partially exposed, the front surface being on a side of the first film base on which side the second film base is present.

With the above configuration, the front surface of the first film base is partially exposed. This makes it easy to visually or in another manner check whether a first film base is present.

The above configuration can thus prevent an operator from, for example, forgetting to attach a first film base.

A separator roll in accordance with an embodiment of the present invention may be configured such that the multilayer label has an end at which a residue-removed portion is present, the residue-removed portion being a portion at which the front surface of the first film base is partially exposed.

The above configuration allows the front surface of the first film base to be partially exposed along an end of the multilayer label easily. The above configuration further makes it possible to, in a case where, for instance, someone handles the separator roll with gloves on, easily peel the second film base off from the first film base by peeling the second film base from the side of the residue-removed portion.

A separator roll in accordance with an embodiment of the present invention may be configured such that the first film base has a color different from a color of the second film base.

With the above configuration, the first film base has a color different from the color of the second film base, which is disposed on the first film base. This allows the first film base to be identified more easily.

A separator roll in accordance with an embodiment of the present invention may be configured such that the nonaqueous electrolyte secondary battery separator has a color different from a color of the first film base.

With the above configuration, the nonaqueous electrolyte secondary battery separator has a color different from the color of the first film base, which is bonded to the nonaqueous electrolyte secondary battery separator. This allows the first film base to be identified even more easily.

A separator roll in accordance with an embodiment of the present invention may be configured such that the multilayer label is attached so as to extend across a longitudinal end of the nonaqueous electrolyte secondary battery separator which longitudinal end is at the outer layer surface.

With the above configuration, the multilayer label is attached so as to extend across an end of the nonaqueous electrolyte secondary battery separator. This allows the end to be fastened with use of the multilayer label.

The above configuration thus eliminates the need to separately use a fastening sticker configured to fasten an end of the nonaqueous electrolyte secondary battery separator, thereby making it possible to omit such a fastening sticker or the like.

A separator roll in accordance with an embodiment of the present invention may further include a fastening sticker configured to fasten a longitudinal end of the nonaqueous electrolyte secondary battery separator which longitudinal end is at the outer layer surface.

The above configuration includes, as a member separate from the multilayer label, a fastening sticker configured to fasten a longitudinal end of the nonaqueous electrolyte secondary battery separator. This increases the degree of freedom in where to attach the multilayer label. The above configuration further makes it possible to attach a multilayer label and a fastening sticker at respective time points different from each other. For instance, the above configuration makes it possible to attach (i) a fastening sticker during the step of winding up the nonaqueous electrolyte secondary battery separator and (ii) a multilayer label during a multilayer label attaching step after the winding step. The above configuration thus makes it possible to attach the multilayer label and the fastening sticker at respective appropriate time points different from each other.

A method in accordance with an embodiment of the present invention for producing a separator roll is a method for producing a separator roll including a separator core and a nonaqueous electrolyte secondary battery separator wound around the separator core and in contact with an outer peripheral surface of the separator core, the method including attaching a multilayer label to an outer layer surface of the nonaqueous electrolyte secondary battery separator wound around the separator core and in contact with the outer peripheral surface, the multilayer label including a plurality of film bases disposed on top of each other, the plurality of film bases including at least one film base detachable from another film base included in the plurality of film bases.

The above method includes a multilayer label attaching step, which is a step of attaching a multilayer label to the outer layer surface of the nonaqueous electrolyte secondary battery separator, the multilayer label including a plurality of film bases, at least one of which is detachable from another film base. The above method is thus a method for producing a separator roll that allows easy identification of information on the production of the separator.

A label checking method in accordance with an embodiment of the present invention is a method for checking a label attached to a separator roll including a separator core and a nonaqueous electrolyte secondary battery separator wound around the separator core and in contact with an outer peripheral surface of the separator core, the method including checking whether a multilayer label is attached to an outer layer surface of the nonaqueous electrolyte secondary battery separator wound around the separator core and in contact with the outer peripheral surface, the multilayer label including a plurality of film bases disposed on top of each other, the plurality of film bases including at least one film base detachable from another film base included in the plurality of film bases.

The above method includes a multilayer label checking step, which is a step of checking whether a multilayer label is attached to the outer layer surface of the nonaqueous electrolyte secondary battery separator, the multilayer label including a plurality of film bases, at least one of which is detachable from another film base. The above method is thus a label checking method suitably usable for a separator roll that allows easy identification of information on the production of the separator.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

REFERENCE SIGNS LIST

1 Lithium-ion secondary battery (nonaqueous electrolyte secondary battery)
5 Core (separator core)
7, 70 Separator roll
8 Multilayer label
9 Fastening sticker
12 Separator
12a Heat-resistant separator (nonaqueous electrolyte secondary battery separator)
14 Outer layer surface
15 End
54 Outer peripheral surface
55 Inner peripheral surface
81 First film base (film base)
81a Front surface
82 Second film base (film base)
83 Residue-removed portion
84 QR Code (information)
85 Bar code (information)
S9 Multilayer label attaching step
S10 Multilayer label checking step

The invention claimed is:
1. A separator roll, comprising:
a separator core;
a nonaqueous electrolyte secondary battery separator wound around the separator core and in contact with an outer peripheral surface of the separator core; and
a multilayer label attached to an outer layer surface of the nonaqueous electrolyte secondary battery separator, the multilayer label including a plurality of film bases disposed on top of each other,
the plurality of film bases including at least one film base detachable from another film base included in the plurality of film bases.
2. The separator roll according to claim 1,
wherein:
the plurality of film bases include (i) a first film base to be bonded to the outer layer surface and (ii) a second film base disposed detachably on the first film base and showing information on the nonaqueous electrolyte secondary battery separator; and
a front surface of the first film base is partially exposed, the front surface being on a side of the first film base on which side the second film base is present.
3. The separator roll according to claim 2,
wherein
the multilayer label has an end at which a residue-removed portion is present, the residue-removed portion being a portion at which the front surface of the first film base is partially exposed.
4. The separator roll according to claim 2,
wherein
the first film base has a color different from a color of the second film base.
5. The separator roll according to claim 2,
wherein
the nonaqueous electrolyte secondary battery separator has a color different from a color of the first film base.

6. The separator roll according to claim 1,
wherein
the multilayer label is attached so as to extend across a longitudinal end of the nonaqueous electrolyte secondary battery separator which longitudinal end is at the outer layer surface.

7. The separator roll according to claim 1, further comprising:
a fastening sticker configured to fasten a longitudinal end of the nonaqueous electrolyte secondary battery separator which longitudinal end is at the outer layer surface.

8. A method for producing a separator roll including a separator core and a nonaqueous electrolyte secondary battery separator wound around the separator core and in contact with an outer peripheral surface of the separator core,
the method comprising
attaching a multilayer label to an outer layer surface of the nonaqueous electrolyte secondary battery separator wound around the separator core and in contact with the outer peripheral surface, the multilayer label including a plurality of film bases disposed on top of each other,
the plurality of film bases including at least one film base detachable from another film base included in the plurality of film bases.

9. A method for checking a label attached to a separator roll including a separator core and a nonaqueous electrolyte secondary battery separator wound around the separator core and in contact with an outer peripheral surface of the separator core,
the method comprising
checking whether a multilayer label is attached to an outer layer surface of the nonaqueous electrolyte secondary battery separator wound around the separator core and in contact with the outer peripheral surface, the multilayer label including a plurality of film bases disposed on top of each other,
the plurality of film bases including at least one film base detachable from another film base included in the plurality of film bases.

* * * * *